US006963065B2

(12) United States Patent
Conti et al.

(10) Patent No.: US 6,963,065 B2
(45) Date of Patent: Nov. 8, 2005

(54) NORMALIZATION APPARATUS FOR PANEL DETECTOR PET SCANNERS

(75) Inventors: Maurizio Conti, Knoxville, TN (US);
James J. Hamill, Knoxville, TN (US);
Michael E. Casey, Knoxville, TN (US);
Mu Chen, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 372 days.

(21) Appl. No.: 10/418,520

(22) Filed: Apr. 18, 2003

(65) Prior Publication Data

US 2004/0206897 A1 Oct. 21, 2004

(51) Int. Cl.[7] ............ G01D 18/00; G12B 13/00
(52) U.S. Cl. .............. 250/252.1; 250/363.03; 250/363.04; 250/370.07; 250/370.1; 250/493.1; 250/494.1; 600/427
(58) Field of Search ............... 250/252.1, 363.04, 250/363.03, 370.07, 307.09, 370.1, 493.1, 494.1; 600/427

(56) References Cited

U.S. PATENT DOCUMENTS

| | | | | |
|---|---|---|---|---|
| 5,502,303 A | * | 3/1996 | Gonzalez-Lepera | 250/252.1 |
| 5,543,622 A | | 8/1996 | Stearns | |
| 6,774,358 B2 | * | 8/2004 | Hamill et al. | 250/252.1 |
| 2004/0021065 A1 | * | 2/2004 | Weber | 250/252.1 |
| 2004/0075048 A1 | * | 4/2004 | Zyromski | 250/252.1 |
| 2005/0023473 A1 | * | 2/2005 | Burr et al. | 250/368 |

FOREIGN PATENT DOCUMENTS

| | | | | | |
|---|---|---|---|---|---|
| JP | | 10002965 A | * | 1/1998 | G01T/1/161 |

OTHER PUBLICATIONS

D. L. Bailey et al., "Quantitative Procedures in 3D PET." The Theory and Practice of 3D PET. B. Bendriem and D. W. Townsend, Eds., Dordrecht, Netherlands: Kluwer Academic Publishers, 55–109 (1998).
D. W. Townsend et al., "Three dimensional reconstruction of PET data from a multi–ring camera," IEEE Trans. Nucl. Sci., vol. 36, No. 1, 1056–1065, (1989).
M. E. Casey et al., "A component based method for normalization in volume PET, " Proc. 3rd. Int. Meeting on Fully Three–Dimentional Image Reconstruction in Radiology and Nuclear Medicine, Aix–les–Bains, France, 67–71. (1995).
R. D. Badawi and P. K. Marsden, "Developments in component–based normalization for 3D PET," Phys. Med. Biol., vol. 44, pp. 571–594, 1999.
J. M. Ollinger, "Detector efficiency and COmpton scatter in fully 3D PET," IEEE Trans. Nucl. Sci., vol. 42, No. 4, pp. 1168–1173, Aug. 1995.
G. German and E. J. Hoffman, "A study of data loss and mispositioning due to pileup in 2–D detectors in PET," IEEE Trans. Nucl. Sci., vol. 37, No. 2, pp. 671–675, Apr. 1990.

* cited by examiner

*Primary Examiner*—David Porta
*Assistant Examiner*—Christine Sung
(74) *Attorney, Agent, or Firm*—Pitts & Brittain, P. C.

(57) ABSTRACT

A normalization apparatus and method for a PET scanner with panel detectors for obtaining an estimate of a normalization array, for correction for count rate effects on the normalization array, and for measurement of the relation between the normalization array and the count rate. The method of the present invention is based on two quasi-independent radial and axial components, which are count rate dependent due to sensitivity changes across the detector blocks. A scatter source is disposed at the center of the FOV and a scatter-free source is disposed at the outer edge of the FOV. The method computes the normalization array through several steps which evaluate the geometric profile, the axial profile, and the correction factor. A count rate correction is introduced to extend the normalization array to any count rate.

19 Claims, 7 Drawing Sheets

NORMALIZATION APPARATUS FOR PANEL DETECTOR PET SCANNERS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to Positron Emission Tomography (PET) scanners having panel detectors. More particularly, this invention pertains to an apparatus and method for obtaining an estimate of a normalization array to correct for count rate effects associated with such a scanner.

2. Description of the Related Art

The application for patent, Ser. No. 10/103,276, filed Mar. 21, 2002, entitled "Normalization Apparatus for PET and SPECT Scanners and Method for Using Same", has at least one common inventor with the present invention. The '276 application is incorporated herein by reference. In that application, it is discussed that various techniques are used for medical imaging. With respect to Positron Emission Tomography (PET), it is recognized that such is popular in radiology because of its ability to non-invasively study physiological processes and structures within the body.

PET is designed to measure the amount of radioactivity along many lines of response (LORs) that pass through the patient and are intercepted by the scanner's detectors. Measurement errors are always present, and in many cases must be corrected by the software that processes the measurements. In particular, the response measured on each LOR is subject to an error in magnitude. Normalization coefficients represent the relationship between the measured and actual magnitude of radiation and are used to correct the magnitude errors. Normalization coefficients are determined by measuring the difference in sensitivity or efficiency of the detectors in the scanners. Normalization of scanner data is usually performed by estimating the sensitivity or efficiency of a LOR.

As discussed by D. L. Bailey et al., "Quantitative Procedures in 3D PET", *The Theory and Practice of 3D PET*, B. Bendriem and D. W. Townsend, Eds., Dordrecht, Netherlands: Kluwer Academic Publishers, 55–109 (1998), the non-uniformity of the different LORs in the sinogram must be corrected with an appropriate normalization in order to reduce artifacts created in a reconstructed image. The current techniques are based on: direct measurements of the normalization array; component-based methods simply using scatter-free $^{68}$Ge rods; and component-based methods using scatter-free $^{68}$Ge rods and methods to calculate or estimate and then subtract the scatter component. However, none of these methods are useful with PET scanners due to the high sensitivity of large area panel detectors.

In direct measurement methods, the elements of a normalization array are proportional to the reciprocal of counts acquired with a uniform source. This technique requires long acquisition time for good statistics in each element of the array. See D. W. Townsend, et al., "Three dimensional reconstruction of PET data from a multi-ring camera", *IEEE Trans. Nucl. Sci.*, vol. 36, no. 1, 1056–1065, (1989). In component-based methods, the normalization array is expressed as a product of factor functions, each being reduced to a much smaller number of parameters, as discussed by M. E. Casey, H. Gadagkar and D. Newport, "A component based method for normalization in volume PET", *Proc. 3rd Int. Meeting on Fully Three-Dimentional Image Reconstruction in Radiology and Nuclear Medicine*, Aix-les-Bains, France, 67–71, (1995).

The lack of usefulness of these conventional methods with PET scanners having panel detectors is due to several factors. First, the PET scanner defines a relatively large field of view (FOV) and has high resolution, which makes it impractical to perform direct measurements of a normalization array. For example, a typical array is comprised of 320×256×3935 elements. The PET scanner further defines a relatively long FOV. Combined with a large tunnel and the absence of septa, the system is sensitive to scatter. Scatter-free sources cannot be used alone. Further, estimating and subtracting the scatter component is not the most effective method. Finally, none of the techniques described corrects for count rate effects, which are relevant for high sensitivity flat panel detectors.

It has been observed that normalization is count rate dependent. As a result, the normalization should be obtained in count rate conditions similar to the clinical scan on which it is applied in order to prevent ring artifacts in the transaxial views and banding in the axial direction.

BRIEF SUMMARY OF THE INVENTION

The present invention is a normalization apparatus and method for a Positron Emission Tomograph (PET) scanner with panel detectors. The normalization apparatus is provided for obtaining an estimate of a normalization array in a reasonable time while using setup and sources that includes a fraction of radiation scattered by the source. The method of the present invention allows for correction for count rate effects on the normalization array and for the measurement of the relation between the normalization array and the count rate. The method of the present invention is based on two quasi-independent radial and axial components, which are count rate dependent due to sensitivity changes across the detector blocks.

The apparatus of the present invention includes a scatter source disposed at the center of the field of view (FOV) and a scatter-free source disposed at the outer edge of the FOV. The scatter source is comprised of a source disposed within a scattering rod. The source of one embodiment is a $^{68}$Ge source is disposed in steel casing and is sealed at each end. In another embodiment, an $^{18}$F source is provided. The scattering rod of one embodiment is a radiation scattering brass rod defining a central cavity is provided for closely receiving the scatter source. The scatter-free source is the source used in association with the scattering rod.

Data is collected using the apparatus of the present invention in four primary steps. First, the $^{68}$Ge source is positioned at the outer edge of the FOV in order to acquire a geometric profile. The position encoding of the scanner detector heads is then inhibited so that the scanner assumes that the detectors are static and that the scatter source is a rotating rod of activity. A long-term acquisition is then performed. Next, the $^{68}$Ge source is positioned at the center of the FOV and within the radiation scattering brass rod. This arrangement is utilized to acquire an axial profile correction. A second long-term acquisition is then performed.

Next, the first step is repeated using the 18F source positioned at the outer edge of the FOV. A third long-term acquisition is performed to produce output in twelve consecutive frames representing one hour each. For each sinogram, the average singles count rate is recorded. Finally, the second step is repeated using the $^{18}$F source positioned at the center of the FOV and within the radiation scattering brass rod. A fourth long-term acquisition is then performed to produce twelve consecutive frames representing one hour each. For each sinogram, the average singles count rate is recorded.

After the data has been collected, a normalization array N is formed. Because the panel detectors rotate around the patient, the normalization array N takes an angle-independent form, and whose factors include: the geometric profile representing the average for each segment, the axial profile, and a correction factor. One set of normalization factors is applied to the combined sinogram of measured radiation. The method of the present invention computes the normalization array N through several steps which evaluate the geometric profile, the axial profile, and the correction factor. Eventually a count rate correction is introduced to extend the normalization array to any count rate.

The geometric transaxial component is obtained by first positioning a line source at the bottom of the FOV. The encoding of the heads position in the data stream is disabled so that the rebinning system assumes that the scanner is not rotating and therefore sees a uniform cylindrical shell of activity.

Normalization coefficients are derived from measured sinograms of known activity distributions. First, the axial profile function is evaluated for sensitivity variations of the uniform source in the axial direction. Given the angularly averaged sinogram obtained with a uniform source having no scatter, $c(z)$ is estimated as the average sensitivity of plane z in a given segment:

$$c(z, seg) = \frac{\sum_r S(r, z, seg)}{\frac{1}{M} \sum_{r,z} S(r, z, seg)},$$

where M is the number of planes in the segment considered.

Then, from the functional form $N=c(z)g(r,seg)$, disregarding at this stage the correction factor, the normalization constraint that the normalized sinogram is a uniform unit array, $N[S]=1$, is imposed. Specifically, the normalized sinogram of the rotating source is equal to unit after performing an arc correction and assuming that in this first approximation the correction factor is equal to 1.

In each segment, an average is performed over all of the planes to obtain an average geometric profile for the segment. Finally, the geometric profile is made symmetrical in the radial direction, adding the geometric profile to its mirror image with respect to the center. The geometric profile is corrected plane by plane using the correction factor. The geometric profile coefficient removes the higher-frequency features due to detector blocks and to the rebinning procedure. However, some residual plane-by-plane low frequency distortions are still present. The observed distortions are fitted to a series of fifteen cosine functions, providing a correction term for normalization.

In the evaluation of the axial and geometric profile described above, a scatter-free acquisition is used. The axial profile of the normalization array is adjusted with a direct and non scatter-free measurement. Using the sinogram collected using the $^{68}$Ge source in the scattering rod, the normalization array is corrected using the equation:

$$N_2(r, z, seg) = N_1(r, z, seg) \cdot \frac{Polfit_{scat}(z, seg)}{Axialprof_{scat}(z, seg)},$$

where $Axialprof_{scat}(z,seg)$ is the axial profile of the sinogram S of the scattering source, and $Polfit^{scat}(z,seg)$ is a second-order polynomial fit to $Axialprof^{scat}(z,seg)$.

Correction is then performed on the radial and axial profiles of the normalization array according to the count rate of the patient sinogram. Normalization is count rate dependent and therefore is obtained in count rate conditions similar to the clinical scan on which it is applied in order to prevent ring artifacts in the transaxial views and banding in the axial direction.

In order to properly correct the normalization for count rate effects, two methods have been devised. In the first method, a normalization array is selected from a database of normalization arrays obtained with sources of different activities, using $^{18}$F over a range of approximately 5 half-lives, or approximately 10 hours. In the second method, the normalization measured at low count rate is extended to a higher count rate using a suitable function.

Correction of a radial profile is performed with the understanding that each radial element of the normalization array changes with count rate. A multiplicative correction factor follows a polynomial function of count rate (singles/block count rate). The correction factor multiplies the normalization array at a low count rate. The twelve normalization arrays discussed above are obtained at different count rates. The average of the radial elements over all the planes of each segment of the normalization array is plotted as a function of singles. The curve is then fitted with a second-order polynomial and the coefficients are stored. A generic normalization array is obtained at count rate equal to zero and is then corrected in the radial profile and adjusted to the proper profile.

Correction of axial profile is accomplished using a procedure similar to that used for radial profile. Averaging in the correction of the axial profile is performed over the radial element of each plane z.

To estimate the correction factor, twelve sinograms are obtained as described above and at different count rates. The average of the axial elements over all the radial elements of each plane is plotted as a function of singles. The curve is then fitted with a second-order polynomial and the coefficients are stored. A generic normalization array is obtained at count rate equal to zero and is then corrected in the axial profile and adjusted to the proper profile.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A normalization apparatus for a Positron Emission Tomograph (PET) scanner with panel detectors is provided in the present invention. The normalization apparatus is provided for obtaining an estimate of a normalization array in a reasonable time while using setup and sources that includes a fraction of radiation scattered by the source. The method of the present invention allows for correction for count rate effects on the normalization array. Further, the method of the present invention allows for the measurement of the relation between the normalization array and the count rate. Using a simple model, the method adjusts the normalization array accordingly to the count rate at which the patient scan was obtained. The method of the present invention requires the count rate relation to be measured only once for a particular apparatus, and can be performed prior to installation in the field.

Figure 1:
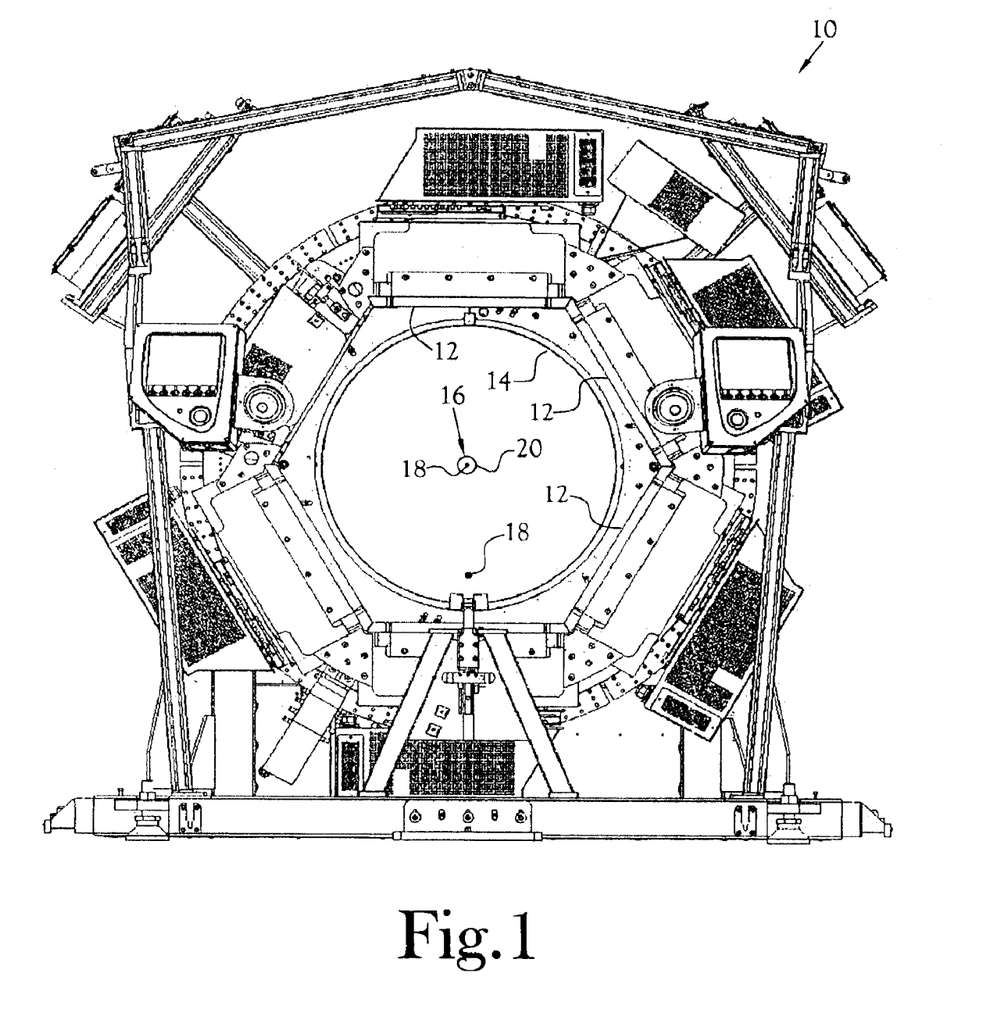
FIG. 1 is an end view of a PET scanner having a circular array of five panel detectors, a first position being indicated for the placement of a scatter-free source and a second position for the placement of a scatter source in accordance with the present invention.

As discussed above, in the PET field, some 3D PET scanners have a large Field of View (FOV) and high resolution. In such situations, a component based method for estimating a normalization array is the most appropriate choice, given the large size of the sinograms. Illustrated in FIG. 1 is a PET scanner 10 having a circular array of five panel detectors 12. The panel detectors 12 are rotated about a gantry 14 in which a patient is positioned, and which defines the FOV. A scatter source 16 is selectively positioned at the center of the gantry 14, and a scatter-free source 18 is selectively positioned at the radial edge of the gantry 14. The rotational symmetry of the scanner 10, because the panel detectors 12 rotate around the patient, allows the normalization array to be expressed in two dimensions, averaging over the angular dimension.

The method of the present invention is based on two quasi-independent radial and axial components, which are separately evaluated in two independent experiments. The method of the present invention takes into account that radial and axial components of the normalization are count rate dependent due to sensitivity changes at the edges of detector blocks.

As indicated above, the present invention incorporates a scatter source 16 disposed at the center of the FOV and a scatter-free source 18 disposed at the outer edge of the FOV. The scatter source 16 is comprised of a source 18 disposed within a scattering rod 20. The source 18 of one embodiment is a $^{68}$Ge source is disposed in steel casing and is sealed at each end. For the PET scanners 10 tested, a scatter source 16 defining a length of 70 cm was used. However, it will be understood that the length of the source is dependent on the length of the patient gantry 14. For testing purposes, a source 18 having an activity range of from 0.1 to 2 mCi. The casing wall is less than 3 mm thick, and the outer diameter is less than or equal to 1.5 cm. The scattering rod 20 of one embodiment is a radiation scattering brass rod defining a central cavity is provided for closely receiving the scatter source. The rod 20 defines a wall thickness of approximately 1.5 cm.

It will be understood that the $^{68}$Ge source as described may be configured in various manners. In any configuration, the thickness and material of fabrication of the casing is selected to limit absorption and scatter to a small fraction (less than 1%) of the emitted gamma rays. It will also be understood that the source activity range and size are selected depending upon the count rate capability of the scanner 10.

Figure 2A:
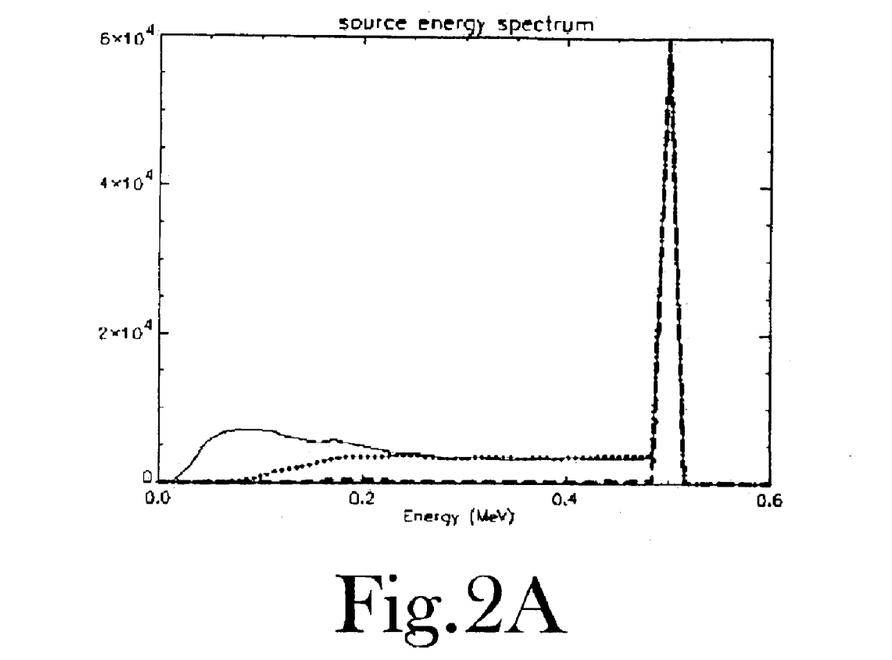
FIG. 2A illustrates a comparison of source energy spectrum from three sources.
Figure 2B:
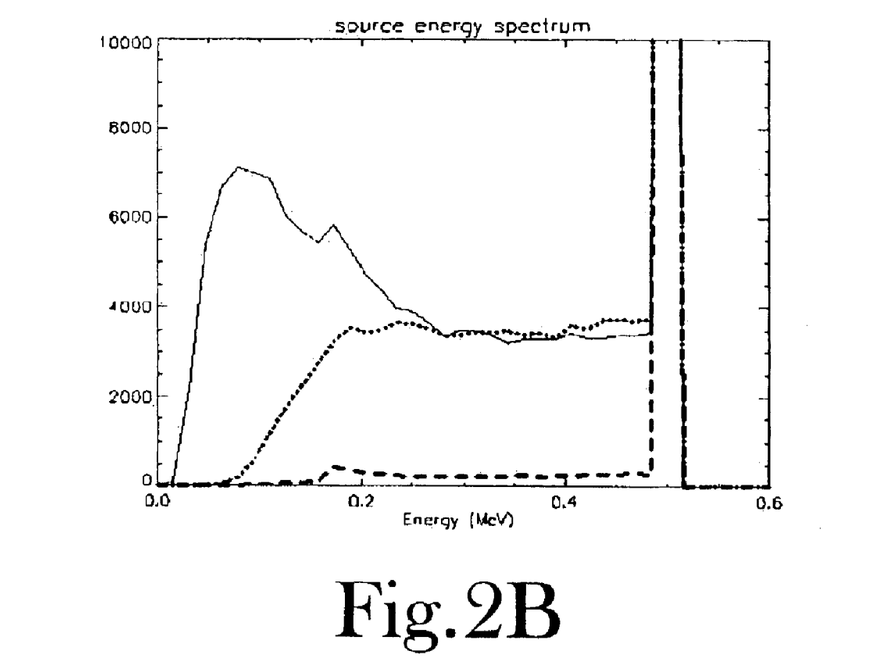
FIG. 2B is an enlarged scale replica of the comparison illustrated in FIG. 2B, better illustrating the spectra in the range 0.3–0.5 MeV.

It will be understood by those skilled in the art that, though the scattering rod 20 has been described as being fabricated from brass, the scattering rod 20 may be alternatively be fabricated from a material other than brass. Materials such as copper and other elements, compounds and alloys may be used, for example. The choice of material and diameter are selected in order to obtain an energy spectrum of the photon escaping the scattering rod with a shape similar to that of a 20 cm diameter water cylinder, or of a simple model of a patient, as best illustrated in FIGS. 2A and 2B. FIG. 2A graphically illustrates a comparison of source spectrum of a water phantom, a 3 cm diameter brass bar, and a 1 mm wall steel rod. FIG. 2B is an enlarged scale replica of the comparison in FIG. 2B better illustrating the comparison of the spectra in the range of 0.3–0.5 MeV.

Further, it will be understood that the scattering rod 20 receiving a positron line source 18 may alternatively be a cylinder filled uniformly with water or other material having an absorption coefficient similar to water, and with activity uniformly distributed therein. This cylinder typically defines a diameter in the range of from approximately 20 cm to approximately 30 cm and a length adapted to extend through the entire axial FOV of the scanner. Alternatively, the cylinder is shorter than the FOV and includes a mechanical assembly to move the source axially inside the FOV of the scanner 10.

The scatter-free source 18 is the source used in association with the scattering rod 20. In addition to the $^{68}$Ge source disclosed above, an $^{18}$F source includes a rigid tube defining and inner diameter of approximately 2 mm. The rigid tube defines substantially the same length as the scatter source. Namely, for testing purposes, the rigid tube defines a length of 70 cm. The rigid tube is then filled with 18F. The rigid tube in the testing was fabricated from plastic.

Data is collected using the apparatus of the present invention in four primary steps. First, the $^{68}$Ge source 18 is positioned at the outer edge of the FOV in order to acquire a geometric profile. The position encoding of the scanner detector heads 12 is then inhibited so that the scanner 10 assumes that the detectors are static and that the source 18 is a rotating rod of activity. A long-term acquisition is performed. The length of the acquisition is dependent on the sensitivity of the scanner 10. The acquisition may require, for example, 24 hours. The output is a sinogram denoted as line.s.

Next, the $^{68}$Ge source 18 is positioned at the center of the FOV and within the radiation scattering brass rod 20. This arrangement is utilized to acquire an axial profile correction. A long-term acquisition is then performed. The length of the acquisition is dependent on the sensitivity of the scanner 10. As before, the acquisition may require, for example, 24 hours. The output is a sinogram denoted as scat.s.

Next, the first step is repeated using the $^{18}$F source 18 positioned at the outer edge of the FOV. The position encoding of the scanner detector heads 12 is then inhibited so that the scanner 10 assumes that the detectors are static and that the scatter source is a rotating rod of activity. A long-term acquisition is performed. The length of the acquisition is dependent on the sensitivity of the scanner 10. The output is twelve consecutive frames denoted as line_n.s. Each frame represents one hour. For each sinogram, the average singles count rate is recorded.

Finally, the second step is repeated using the $^{18}$F source 18 positioned at the center of the FOV and within the radiation scattering brass rod 20. A long-term acquisition is then performed. The length of the acquisition is dependent on the sensitivity of the scanner 10. The output is twelve consecutive frames denoted as scat_n.s. Each frame represents one hour. For each sinogram, the average singles count rate is recorded.

After the data has been collected, a normalization array N is formed. Because the panel detectors rotate around the patient, the normalization array N takes an angle-independent form:

$$N(lowcountrate) = \frac{1}{g(r, seg) \cdot f(r, z, seg) \cdot c(z, seg)}$$

where g(r,seg) is the geometric profile representing the average for each segment, c(z,seg) is the axial profile, and f(r,z,seg) is a correction factor. Further, r is the radius, z is the axial position, and seg is the segment of the 3D sinogram. The correction term f contains only low radial frequencies. The g and f terms are derived from a scan of a line source moving relative to the detectors. The c term is derived from a scan of an activity-filled uniform cylindrical phantom that scatters radiation. In principle, the scatter and the trues require different normalization factors. However, in the present invention, one set of normalization factors is applied to the combined sinogram of measured radiation. The method of the present invention computes the normalization array N through several steps which evaluate the functions g(r,seg), c(z,seg), and f(r,z,seg). Eventually a count rate correction is introduced to extend the normalization array to any count rate.

The geometric transaxial component g(r,seg) is obtained using one of several methods. In one method, a static acquisition of a plane source between the two heads, or a line source moved in a plane, is used. In another method, a line source located at the bottom of the FOV is used. The encoding of the heads position in the data stream is disabled. As disclosed above, the rebinning system then assumes that the scanner is not rotating and therefore sees a uniform cylindrical shell of activity. Each of these methods assumes a uniform scatter free source, and the activity seen by each line of response (LOR) is corrected based on the geometry of the source. Each LOR views the same activity after geometric correction and responds uniformly.

The normalization method of the present invention has been tested on two different scanners. The first scanner is a 2-head scanner having a sinogram size 256 radial positions, 167 direct planes, and 256 angular views. The 2-head scanner has a span of 7, a maximum ring difference of 66, and includes 19 segments for a total of 2021 direct and oblique planes. The second scanner is a 5-head scanner with sinogram size 320 radial positions, 239 direct planes, and 256 angular views. The 5-head scanner has a span of 7, a maximum ring difference of 87, and includes 25 segments for a total of 3935 planes.

Figure 3A:
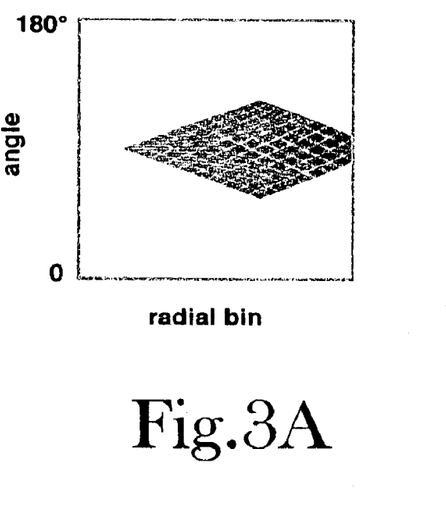
FIG. 3A is a sinogram acquired using a plane source in a two-head PET scanner.
Figure 3B:
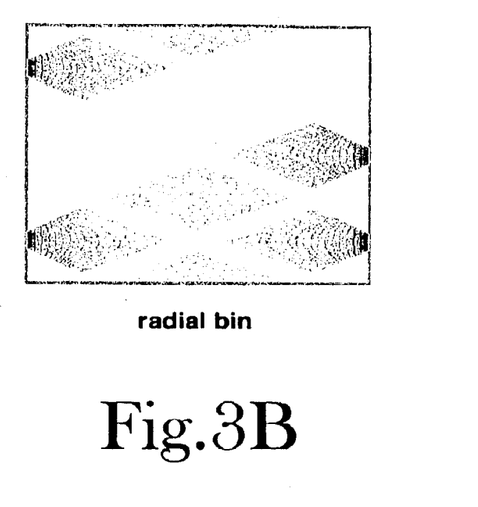
FIG. 3B is a sinogram acquired using a simulated cylindrical shell source in a five-head scanner.

Illustrated in FIGS. 3A and 3B are (r,φ) sinograms—one of the direct planes—for the two-head scanner and the five-head scanner, respectively. The typical "diamonds" of a static panel detector scanner are seen. The sinogram illustrated in FIG. 3A was acquired simulating a plane source, while the sinogram illustrated in FIG. 3B was acquired simulating a cylindrical shell source, thereby causing more counts at the radial edge of FOV.

Figure 3C:
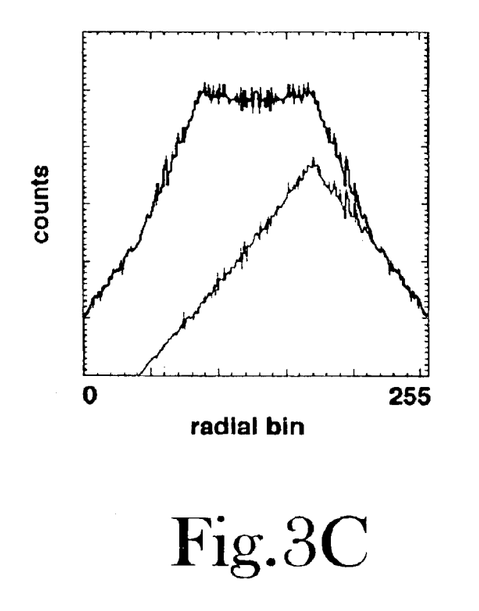
FIG. 3C illustrates a sinogram of the stationary scanner corresponding to that illustrated in FIG. 3A added along the angular dimension, illustrated by the lower signal, and added along the angular dimension after averaging over all the possible rotational positions of the scanner heads, illustrated by the upper signal.
Figure 3D:
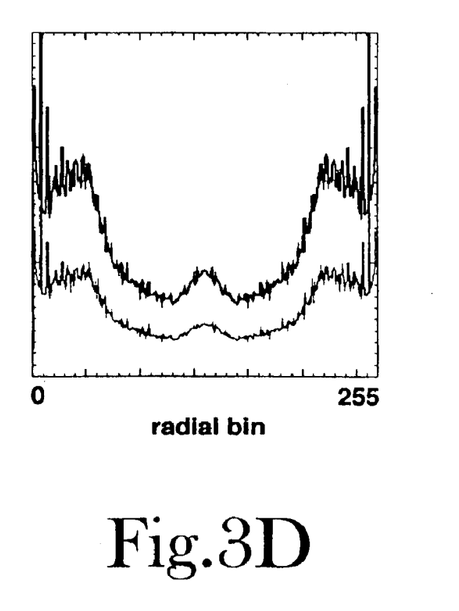
FIG. 3D illustrates a sinogram of the stationary scanner corresponding to that illustrated in FIG. 3B added along the angular dimension, illustrated by the lower signal, and added along the angular dimension after averaging over all the possible rotational positions of the scanner heads, illustrated by the upper signal.

FIGS. 3C and 3D represent the corresponding two sinograms of the scanners added along the angular dimension, illustrated by the lower signal, and added along the angular dimension after averaging over all the possible rotational positions of the scanner heads, illustrated by the upper signal. This latter function represents the geometric or radial profile g(r,z,seg), and is obtained by averaging the sinogram over all measured angles, and adding the result to itself after reflection around the center.

The normalization coefficients are derived from measured sinograms of known activity distributions. First, the axial profile function c(z,seg) is evaluated for sensitivity variations of the uniform source in the axial direction. Given the angularly averaged sinogram S(r,z), obtained with a uniform source having no scatter, c(z) is estimated as the average sensitivity of plane z in a given segment:

$$c(z, seg) = \frac{\sum_r S(r, z, seg)}{\frac{1}{M}\sum_{r,z} S(r, z, seg)},$$

where M is the number of planes in the segment considered.

Then, from the functional form N=c(z,seg)*g(r,seg), disregarding at this stage the correction factor f(r,z,seg), the normalization constraint that the normalized sinogram is a uniform unit array, N[S ]=1, is imposed. Specifically, the normalized sinogram S of the rotating source (line.s) is equal to unit, after performing an arc correction and assuming that in this first approximation the function f is equal to 1, as defined by:

$$1 = N \cdot S(r, z, seg) = \frac{1}{c(z, seg) \cdot g(r, seg)} S(r, z, seg),$$

where:

$$g(r, seg) = \frac{1}{c(z, seg)} S(r, z, seg).$$

In each segment, an average is performed over all of the planes to obtain an average geometric profile for the segment as defined by:

$$g(r, seg) = \frac{1}{M} \sum_{z=0}^{M-1} \frac{1}{c(z, seg)} S(r, z, seg).$$

Finally, g is made symmetrical in the radial direction, adding the function g to its mirror image with respect to the center.

The geometric profile g is corrected plane by plane using the function f. The g coefficient removes the higher-frequency features due to detector blocks and to the rebinning procedure. However, g is an average geometric profile over all the planes in a given segment, and some residual plane-by-plane low frequency distortions are still present. The observed distortions are fitted to a series of fifteen cosine functions, providing the correction term f(r,z,seg). The normalization is therefore corrected using:

$$N_1(r, z, seg) = \frac{N(r, z, seg)}{\sum_{k=0}^{15} a_k(z, seg) \cdot \cos\left(2\pi k \frac{r}{n_{bins}}\right)},$$

where $n_{bins}$ is the number of radial bins in the sinogram.

Figure 4A:
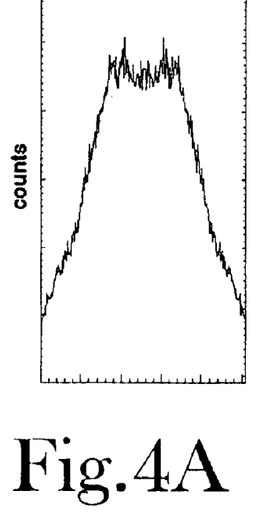
FIG. 4A illustrates a radial profile of a sinogram of a uniform plane source before normalization.
Figure 4B:
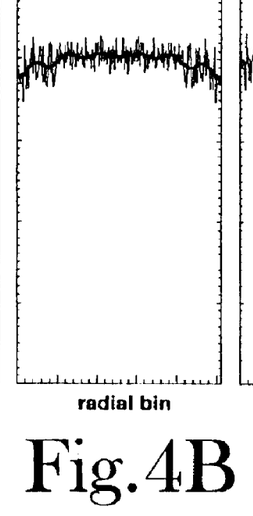
FIG. 4B illustrates the radial profile of the sinogram of FIG. 4A after normalization with the g radial factor.
Figure 4C:
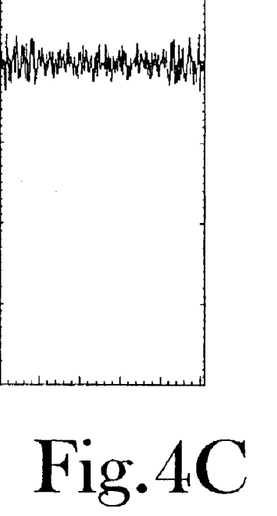
FIG. 4C illustrates the radial profile of the sinogram of FIG. 4A after removal of low-frequency distortions with an f factor.

This procedure is illustrated in FIGS. 4A–4C which is a radial profile of a typical plane, or sinogram of a uniform plane source, before normalization (FIG. 4A), after normalization with the g radial factor (FIG. 4B), and after removal of low-frequency distortions with the f factor (FIG. 4C).

The axial profile is corrected using a scattering source. In the evaluation of the axial and geometric profile, a scatter-free acquisition is used. A realistic scan includes a large fraction of scattered events, which affect the axial profile of the normalization. It is therefore necessary to adjust the axial profile of the normalization array with a direct and non scatter-free measurement of the additional factor c(z,seg).

Figure 5:
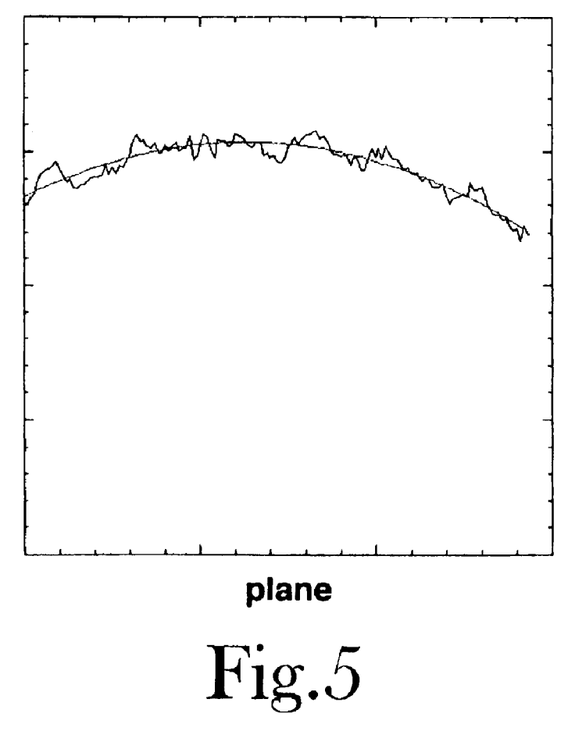
FIG. 5 illustrates an axial profile of the sinogram of the scattering source at segment 0 with a polynomial fit plotted over the sinogram profile.

Using the sinogram collected using the $^{68}$Ge source in the scattering rod, the normalization array is corrected using the equation:

$$N_2(r, z, seg) = N_1(r, z, seg) \cdot \frac{Polfit_{scat}(z, seg)}{Axialprof_{scat}(z, seg)},$$

where $Axialprof_{scat}(z,seg)$ is the axial profile of the sinogram S of the scattering source, and $Polfit_{scat}(z,seg)$ is a second-order polynomial fit to $Axialprof_{scat}(z,seg)$. FIG. 5 illustrates an axial profile of the sinogram of the scattering source (segment 0) and a polynomial fit plotted over the sinogram profile.

Figure 6A:
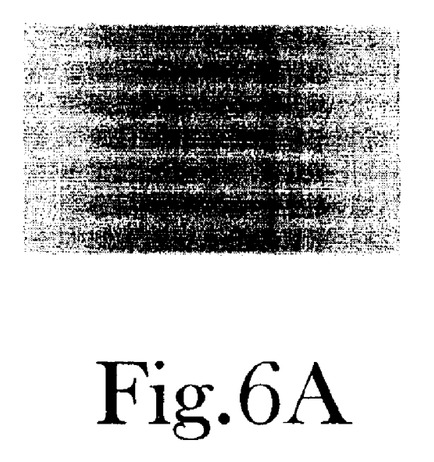
FIG. 6A illustrates a non-normalized, angle-averaged segment-0 sinogram of the plane source.
Figure 6B:
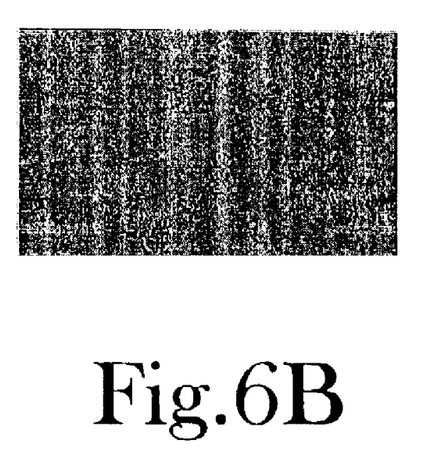
FIG. 6B illustrates normalization of the sinogram of FIG. 6A with the g radial factor.
Figure 6C:
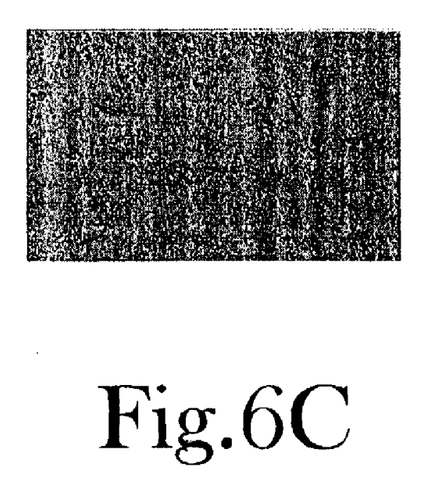
FIG. 6C illustrates removal of low-frequency distortions from the sinogram of FIG. 6B using the f factor.
Figure 6D:
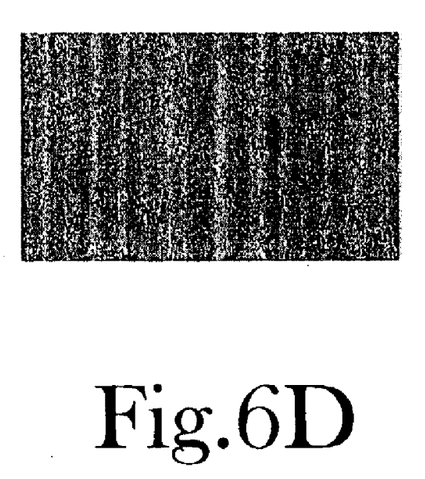
FIG. 6D illustrates the sinogram of FIG. 6C after axial profile adjustment.

Illustrated in FIGS. 6A–6D is an angle-averaged segment-0 sinogram of a plane source after applying different steps of normalization. The vertical direction in each image is the axial direction and the horizontal direction is the radial direction. FIG. 6A illustrates a non-normalized sinogram of the plane source. FIG. 6B illustrates normalization with the g radial factor. FIG. 6C illustrates removal of low-frequency distortions with the f factor. Finally, FIG. 6D illustrates a sinogram after axial profile adjustment.

Correction is then performed on the radial and axial profiles of the normalization array according to the count rate of the patient sinogram. Normalization is count rate dependent and therefor is obtained in count rate conditions similar to the clinical scan on which it is applied in order to prevent ring artifacts in the transaxial views and banding in the axial direction.

Since the normalization array is usually evaluated at low count rate, at higher count rate the scanner response changes, both in the geometric profile and the axial profile. In the case of panel detectors based on blocks of crystals, this difference is attributed to signal pile-up that creates a distortion of the apparent sensitivity of the block, "pushing" detected events toward the center of the block.

Figure 7A:
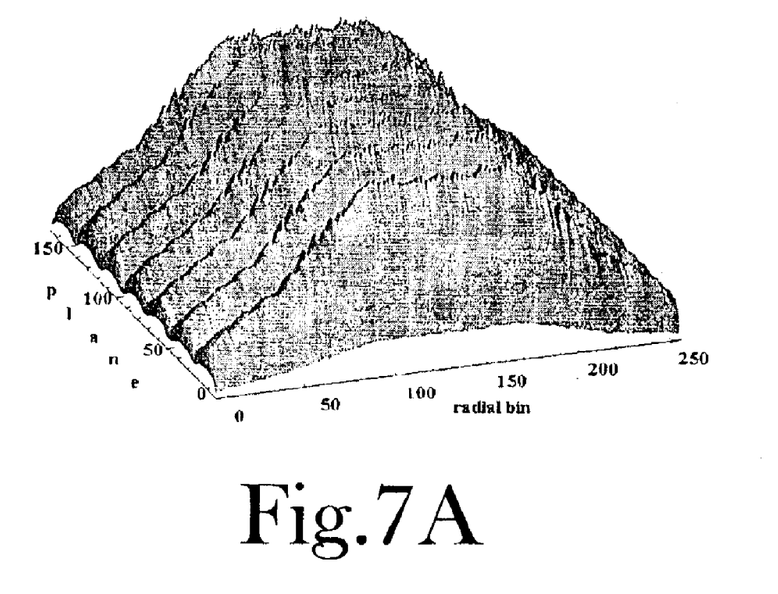
FIG. 7A illustrates a 3D plot of the normalization array segment 0 of a two-head scanner.
Figure 7B:
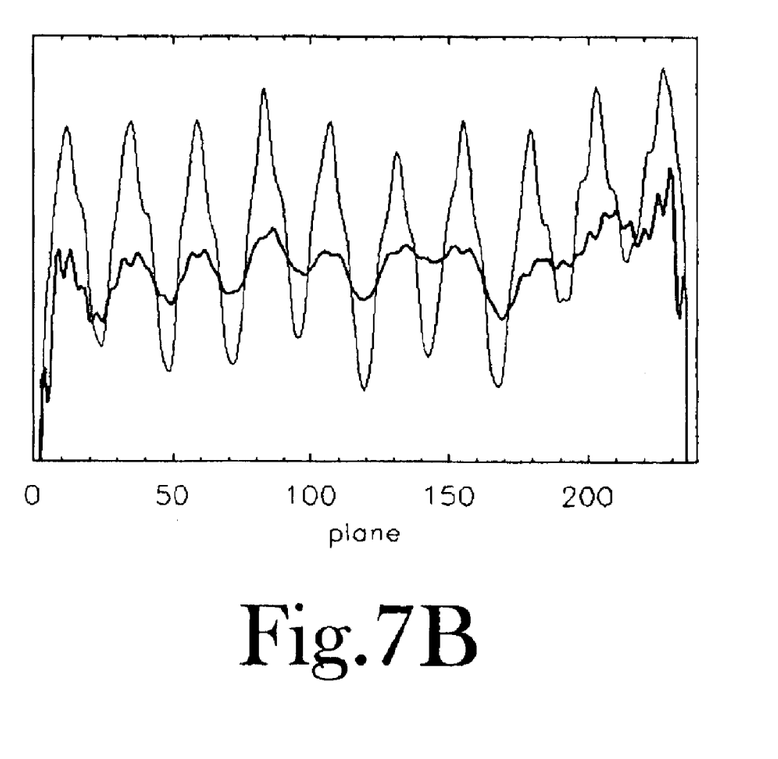
FIG. 7B illustrates the normalization axial profile corresponding to the normalization array of FIG. 7A, plotted as a function of the plane number for two normalization samples taken with different activities.

Count rate dependence is strong in the axial profile where the block structure is only partially corrected if count rate is not accounted for, but less sensitive in the radial direction, where averaging over many LORs takes place. In FIG. 7A, a 3D plot of the normalization array is shown for segment 0 of a 2-head scanner. The block structure in the axial direction is visible in the alternating peak-valley structure. The depth of the peak/valley ratio increases with count rate using an average block singles count rate as a measure of count rate. As illustrated in FIG. 7B, the normalization axial profile is plotted as a function of the plane number for two normalization samples taken with different activities. The first curve, with greater variations, was obtained with a measured count rate per block of 60,000 cps. The second curve was obtained at a singles count rate of 10,000 cps per block. In FIG. 7B a 5-head scanner with a larger axial coverage was used, wherein 10 detector blocks are visible as opposed to 7 as in the scanner used to obtain the profile in FIG. 7A.

In order to properly correct the normalization for count rate effects, two methods have been devised. In the first method, a normalization array is selected from a database of normalization arrays obtained with sources of different activities, using $^{18}$F over a range of approximately 5 half-lives, or approximately 10 hours.

In the second method, the normalization measured at low count rate is extended to a higher count rate using suitable functions $f_R(r,seg,CR)$ for the geometric profile and $f_A(r,seg, CR)$ for the axial profile, which are derived from experimental measurements.

More specifically, correction of a radial profile is performed with the understanding that each radial element of the normalization array N'(r,z,seg) changes with count rate. A multiplicative correction factor $f_R$ is, in one embodiment, described as a polynomial function of count rate (singles/block count rate). The correction factor f multiplies the normalization array at low count rate $N_O$(r,z,seg) as follows:

$$N'(r,z,\text{seg},CR)=f_R(CR,r,z,\text{seg})*N_o(r,z,\text{seg}).$$

The present method estimates f as an average function for each segment and therefore:

$$N'(r,z,\text{seg},CR)=f'_R(CR,r,\text{seg})*N_0(r,z,\text{seg}).$$

To estimate $f_R$, the sinograms line_n.s are obtained as described above. The twelve normalization arrays are obtained at different count rates N(r,z,seg,CR). The average of the radial elements over all the planes of each segment of <N(r,z,seg,CR)>$_z$ is plotted as a function of singles. The curve is fitted with a second-order polynomial:

$$<N(r,z,\text{seg},CR)>_z=f'_R=a_0(r,\text{seg})+a_1(r,\text{seg})*CR+a_2(r,\text{seg})*CR^2.$$

The coefficients are then stored. Specifically, three parameters for each radial element of each segment are stored.

A generic normalization array N(r,z,seg) obtained at count rate CR=0 is then corrected in the radial profile and adjusted to the proper profile at count rate CR:

$$N'(r,z,\text{seg},CR) = N(r,z,\text{seg}) * \frac{f'_R(CR, r, \text{seg})}{f'_R(CR = 0, r, \text{seg})}.$$

Correction of axial profile is accomplished using a procedure similar to that used for radial profile. Averaging in the correction of the axial profile is performed over the radial element of each plane z.

To estimate $f'_A$, the sinograms scat_n.s are obtained as described above. The twelve axial profiles are obtained at different count rate N(r,z,seg,CR). The average of the axial elements over all the radial elements of each plane <N(r,z,seg,CR)>$_r$ is plotted as a function of singles. The curve is fitted with a second-order polynomial:

$$<N(r,z,\text{seg},CR)>_r=f'_A=a_0(z,\text{seg})+a_1(z,\text{seg})*CR+a_2(z,\text{seg})*CR^2.$$

The coefficients are then stored. Specifically, three parameters for each axial element of each segment are stored.

A generic normalization array N(r,z,seg), obtained at count rate CR=0 is then corrected in the axial profile and adjusted to the proper profile at count rate CR:

$$N'(r,z,\text{seg},CR) = N(r,z,\text{seg}) * \frac{f'_A(CR, z, \text{seg})}{f'_A(CR = 0, z, \text{seg})}.$$

While the count rate measurement is described as a singles count rate per block, it will be understood by those skilled in the art the count rate measurement may alternatively be made using other known methods such as a randoms count rate, a prompts count rate, and a net trues count rate.

Further, while the count rate correction as disclosed uses a second-order polynomial function for each element of the normalization array, it will be understood that other functions are useful for performing the same fit. An alternative method use a single function to approximate the low frequency portion of the whole radial (one for each plane) or axial profile (one for each segment), and fit the experimental data accordingly. For example, for the axial profile the function:

$$\gamma=a_0(\text{seg},CR)+a_1(\text{seg},CR)*z+\cos(kz+\psi)$$

may be used, where k is given by the block geometry, $\psi$ is a quasi constant value, and $a_0$ and $a_1$ are functions obtained through experimentation.

A further alternative method is to factorize the axial profile into several components. Specifically, the axial profile is factorized into line-of-response density, detector block sensitivity, and a residual component. The line-of-response density factor is related to the sinogram formation, and is corrected by:

$$\text{Axialprof}(z,\text{seg},CR)=\text{Axialprof}(z,\text{seg},CR=\text{low})*(1+k(-1)^z),$$

where k is a measured parameter.

In this method, detector block sensitivity of each block I is modeled as a Gaussian function:

$$Gaus_{blockI} = A_0(CR) * e^{\frac{-(z-A_1(CR))^2}{A_2^2(CR)}}$$

for each block structure, and the resulting total block structure is Gaus(z,CR), the sum of these Gaussian functions.

After dividing the Axialprof(z,seg,CR) by Gaus(z,CR), the residuals $Rs_1$ are divided by the smallest residual to obtain second order residuals $Rs_2$. The second order residuals have the relationship:

$$\frac{Rs_2(z, CR) - 1}{Rs_2(z, CR = \text{low}) - 1} = \frac{stddev(Rs_2(z, CR))}{stddev(Rs_2(z, CR = \text{low}))},$$

where stddev is the standard deviation, and Rs2(z,CR) is the second order residual of the scan at count rate CR. The fittings of (A0, A1, A2) and stddev($Rs_2$(z,CR)) to the singles rates are stored, and the first order residuals are stored. These values are then used to scale the standard axial normalization according to the count rate of the scan to be normalized.

Figure 8:
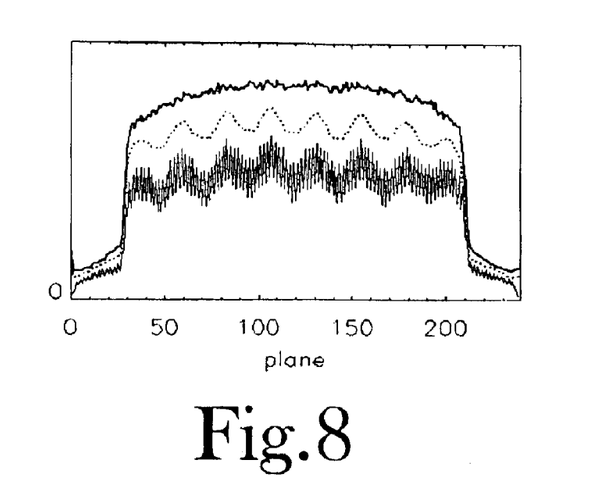
FIG. 8 illustrates an axial profile for a uniform cylindrical source with high activity with various degrees of normalization having been applied.

FIG. 8 illustrates an axial profile for a uniform cylindrical source with high activity with various degrees of normalization having been applied. Namely, illustrated are a non-normalized profile, a normalized profile that has not been corrected for count rate, and a normalized profile that has been corrected for count rate using the method of the present invention. When the standard low count rate normalization is applied, the high frequency structures are completely corrected and the block structure is only partially corrected. A properly count-rate-corrected normalization instead produces a smooth axial profile with no visible block structure. The bulge in the axial profile is mainly due to scatter.

Figure 9A:
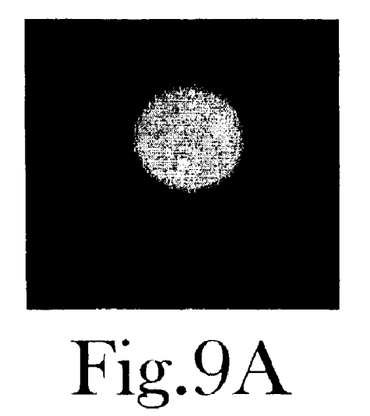
FIG. 9A illustrates a transaxial view of an image reconstructed using a normalization non-count-corrected method.
Figure 9B:
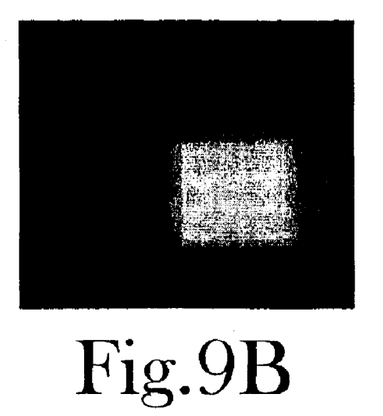
FIG. 9B illustrates an axial view of the image in FIG. 8A reconstructed using a normalization non-count-corrected method illustrated.
Figure 10A:
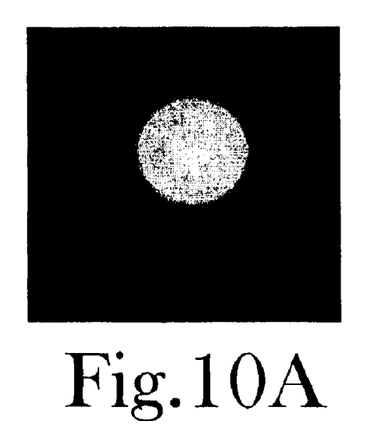
FIG. 10A illustrates a transaxial view of an image reconstructed using a normalization properly count rate corrected.
Figure 10B:
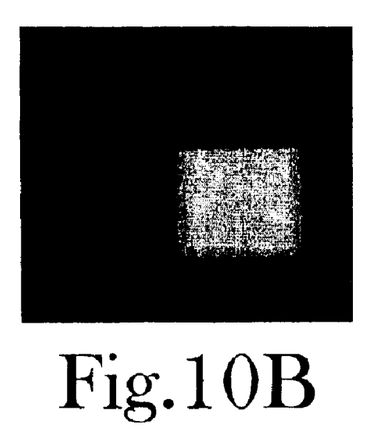
FIG. 10B, illustrates an axial view of the image in FIG. 10A reconstructed using a normalization properly count rate corrected method illustrated.

With a proper count-rate-corrected normalization, normalization-related artifacts, such as ring artifacts and axial banding, disappear. In FIGS. 9A, 9B, 10A and 10B, the effect of the count-rate-correction on the reconstructed images is illustrated. FIG. 9A illustrates a transaxial view of an image reconstructed using a normalization non-count-corrected method. In comparison, FIG. 10A illustrates a transaxial view of an image reconstructed using a normalization properly count rate corrected. FIGS. 9B and 10B are the corresponding axial views. The same cylindrical phantom was used for each acquisition. The cylindrical phantom included cold and hot spheres in a hot background with a 4:1 activity ratio between the spheres and the background. All planes were added in the transaxial view and all sagittal bins were added in the coronal view to enhance the normalization artifacts.

From the foregoing description, it will be recognized by those skilled in the art that a component-based normalization method for revolving panel detector PET scanners has been provided. The method of the present invention is based on separable geometric and axial components. A normalization apparatus is provided for obtaining an estimate of a normalization array in a reasonable time while using setup and sources that includes a fraction of radiation scattered by the source. The method of the present invention allows for correction for count rate effects on the normalization array and for the measurement of the relation between the normalization array and the count rate.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A normalization apparatus for a Positron Emission Tomograph (PET) scanner having panel detectors configured to rotate about a patient gantry, the patient gantry defining a Field of View (FOV), said apparatus comprising:
   a first scatter source including a first radioactive component and being selectively positioned at a center of said FOV;
   a second scatter source including a second radioactive component and being selectively positioned at said center of said FOV;
   a first scatter-free source selectively positioned at a radial edge of said FOV; and
   a second scatter-free source selectively positioned at said radial edge of said FOV, wherein only one of said first scatter source, said second scatter source, said first scatter-free source and said second scatter-free source is selectively positioned within said FOV during an acquisition.

2. The normalization apparatus of claim 1 wherein each of said first scatter source, said second scatter source, said first scatter-free source and said second scatter-free source defines a line source disposed in parallel with a longitudinal axis of said gantry.

3. The normalization apparatus of claim 2 wherein said first scatter source includes said first scatter-free source disposed within a scattering rod, and wherein said second scatter source includes said second scatter-free source disposed within said scattering rod.

4. The normalization apparatus of claim 3 wherein said first radioactive component contains $^{68}$Ge, and wherein said second radioactive component contains $^{18}$F.

5. The normalization apparatus of claim 3 wherein said scattering rod is a radiation scattering brass rod defining a central cavity adapted to closely receive said scatter source.

6. A method for correcting a normalization array for count rate effects, said method being used in association with a normalization apparatus for a Positron Emission Tomograph (PET) scanner having panel detectors configured to rotate about a patient gantry, the patient gantry defining a Field of View (FOV), said apparatus including at least a first scatter source selectively positioned at a center of said FOV, a second scatter source selectively positioned at said center of said FOV, a first scatter-free source selectively positioned at a radial edge of said FOV, and a second scatter-free source selectively positioned at said radial edge of said FOV, wherein only one of said first scatter source, said second scatter source, said first scatter-free source and said second scatter-free source is selectively positioned within said FOV during an acquisition, said method comprising the steps of:

A) positioning said first scatter-free source at the radial edge of the FOV;
B) inhibiting position encoding functions of the scanner panel detectors;
C) acquiring a sinogram to compute a geometric profile;
D) removing said first scatter-free source from within the FOV;
E) enabling position encoding functions of the scanner panel detectors;
F) positioning said first scatter source at the center of the FOV;
G) acquiring a sinogram to compute an axial profile correction;
H) removing said first scatter source from within the FOV;
I) positioning said second scatter-free source at the radial edge of the FOV;
J) inhibiting position encoding functions of the scanner panel detectors;
K) acquiring a series of sinograms to compute a series of geometric profiles;
L) recording an average singles count rate for each of said series of geometric profile sinograms;
M) removing said second scatter-free source from within the FOV;
N) enabling position encoding functions of the scanner panel detectors;
O) positioning said second scatter source at the center of the FOV;
P) acquiring a series of sinograms to compute a series of axial profiles;
Q) recording an average singles count rate for each of said series of axial profile sinograms;
R) removing said second scatter source from within the FOV; and
S) forming a normalization array.

7. The method of claim 6 wherein in said step of forming a normalization array N, said normalization array N is formed in an angle-independent form defined by:

$$N(lowcountrate) = \frac{1}{g(r, seg) \cdot f(r, z, seg) \cdot c(z, seg)}$$

wherein g(r,seg) is said geometric profile, wherein c(z,seg) is said axial profile, wherein f(r,z,seg) is a correction factor, wherein r is a radius of said FOV, wherein z is an axial position, and wherein seg is a segment of a sinogram.

8. The method of claim 6 further including the step of introducing a count rate correction to extend said normalization array to any count rate.

9. The method of claim 7 wherein said axial profile function c(z,seg) is estimated as an average sensitivity of plane z in a given segment:

$$c(z, seg) = \frac{\sum_r S(r, z, seg)}{\frac{1}{M} \sum_{r,z} S(r, z, seg)},$$

where M is a number of planes considered in said segment.

10. The method of claim 9 further including the step of performing an average in each said segment over all planes to obtain an average geometric profile for said segment as defined by:

$$g(r, seg) = \frac{1}{M} \sum_{z=0}^{M-1} \frac{1}{c(z, seg)} S(r, z, seg),$$

wherein g is a geometric profile.

11. The method of claim 10 further including the step of making said geometric profile g symmetrical in said radial direction, said step of making said geometric profile g symmetrical including the step of adding said geometric profile g to a mirror image of said geometric profile g with respect to a center of said geometric profile g.

12. The method of claim 11 further including the step of estimating said normalization array N as:

$$N = \frac{1}{g(r, seg) * c(z, seg)}.$$

13. The method of claim 12 further including the step of correcting said normalization array N using:

$$N_1(r, z, seg) = \frac{N(r, z, seg)}{\sum_{k=0}^{15} a_k(z, seg) \cdot \cos\left(2\pi k \frac{r}{n_{bins}}\right)},$$

where $n_{bins}$ is a number of radial bins in said normalization array.

14. The method of claim 13 further including the step of correcting said axial profile of said normalization array for scatter using the equation:

$$N_2(r, z, seg) = N_1(r, z, seg) \cdot \frac{Polfit_{scat}(z, seg)}{Axialprof_{scat}(z, seg)},$$

where $Axialprof_{scat}(z,seg)$ is an axial profile of said sinogram of said scattering source acquired in said step of acquiring a sinogram to compute an axial profile correction, and $Polfit_{scat}(z,seg)$ is a second-order polynomial fit to said axial profile.

15. The method of claim 7 further including the steps of:
 i) correcting said radial profile of said normalization array according to a count rate of a patient sinogram; and
 ii) correcting said axial profile of said normalization array according to the count rate of the patient sinogram.

16. The method of claim 15 wherein said step of correcting said axial profile of said normalization array is accomplished using:

$$N(r, z, seg, CR) = N(r, z, seg, CR = low) * \frac{f_A(z, seg, CR)}{f_A(z, seg, CR = low)},$$

where CR is said count rate expressed as an average of singles per block in said PET scanner, wherein N(r,z,seg,CR) is obtained for each said CR as $N_2$(r,z,seg) in said step of correcting said axial profile of said normalization array for scatter, and wherein $f_A$ is a function determined using said series of sinograms obtained in said step of acquiring a series of sinograms to compute a series of axial profiles.

17. The method of claim 15 wherein said step of correcting said radial profile of said normalization array is accomplished using:

$$N(r, z, seg, CR) = N(r, z, seg, CR = low) * \frac{f_R(z, seg, CR)}{f_R(z, seg, CR = low)},$$

where CR is said count rate expressed as an average of singles per block in said PET scanner, wherein N(r,z,seg,CR) is obtained for each said CR as $N_2$(r,z,seg) in said step of correcting said axial profile of said normalization array for scatter, and wherein $f_R$ is a function determined using said series of sinograms obtained in said step of acquiring a series of sinograms to compute a series of geometric profiles.

18. The method of claim 15 wherein said step of correcting said axial profile of said normalization array is accomplished using:

$$\gamma = \sum_r N(r, z, seg, CR)$$
$$= a_0(seg, CR) + a_1(seg, CR) * z + \cos(kz + \psi)$$

where γ represents said axial profile, where κ is given by a block geometry, ψ is a quasi constant value, and $a_0$ and $a_1$ are functions determined using said series of sinograms obtained in said step of acquiring a series of sinograms to compute a series of axial profiles.

19. The method of claim 15 wherein said step of correcting said axial profile of said normalization array is accomplished using:

$$Axialprof(z, seg, CR) = Axialprof(z, seg, CR = low) * \frac{Gaus(z, CR)}{Gaus(z, CR = low)} *$$
$$\frac{(Rs_2(z, CR = high) - 1) * h(CR)/h(CR = high) + 1}{(Rs_2(z, CR = high) - 1) * h(CR = low)/h(CR = high) + 1}$$

where:

$$Axialprof(z, seg, CR) = \sum_r N(r, z, seg, CR);$$

$$Gaus(z, CR) = A_0(CR) * e^{\frac{-(z - A_1(CR))^2}{A_2^2(CR)}};$$

$$Rs_2(z, CR = high) = \frac{Axialprof(z, seg, CR = high)}{Gaus(z, CR = high)} * \frac{Gaus(z, CR = low)}{Axialprof(z, seg, CR = low)};$$

h(CR) is the standard deviation of $Rs_2$(z,CR); CR=high represents a highest count rate of an acquired database; and CR=low represents a lowest count rate of said acquired database.

* * * * *